United States Patent
Schrapp et al.

(10) Patent No.: US 12,150,798 B2
(45) Date of Patent: Nov. 26, 2024

(54) X-RAY RADIATION DETECTION

(71) Applicant: Siemens Healthcare GmbH, Erlangen (DE)

(72) Inventors: Michael Schrapp, Munich (DE); Dubravka Ukalovic, Nuremberg (DE); Erick Arruda Camara Ferreira, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 245 days.

(21) Appl. No.: 17/955,047

(22) Filed: Sep. 28, 2022

(65) Prior Publication Data
US 2023/0103195 A1 Mar. 30, 2023

(30) Foreign Application Priority Data

Sep. 30, 2021 (EP) .................................... 21200175

(51) Int. Cl.
*A61B 6/42* (2024.01)
*A61B 6/00* (2024.01)

(52) U.S. Cl.
CPC .......... *A61B 6/4241* (2013.01); *A61B 6/5205* (2013.01)

(58) Field of Classification Search
CPC .... A61B 6/4241; A61B 6/5205; G01T 1/2985
See application file for complete search history.

(56) References Cited

U.S. PATENT DOCUMENTS

| 9,164,183 | B2 | 10/2015 | Kraft et al. | |
| 11,166,683 | B2* | 11/2021 | Carbonne Dit Leychert Garenne | A61B 6/502 |
| 11,559,269 | B2* | 1/2023 | Nakai | G06N 3/006 |
| 12,033,324 | B2* | 7/2024 | Khan | G06V 10/776 |
| 2017/0105698 | A1 | 4/2017 | Kaepplinger et al. | |
| 2019/0150864 | A1 | 5/2019 | Flohr et al. | |
| 2021/0085272 | A1 | 3/2021 | Flohr et al. | |
| 2021/0113178 | A1* | 4/2021 | Zhou | A61B 6/54 |
| 2021/0186439 | A1 | 6/2021 | Goederer et al. | |
| 2022/0308242 | A1* | 9/2022 | Wang | G01T 1/17 |
| 2022/0409159 | A1* | 12/2022 | Freiman | A61B 6/482 |

(Continued)

FOREIGN PATENT DOCUMENTS

| DE | 102019209341 A1 | 12/2020 |
| EP | 3485815 A1 | 5/2019 |

(Continued)

*Primary Examiner* — David P Porta
*Assistant Examiner* — Gisselle M Gutierrez
(74) *Attorney, Agent, or Firm* — Harness, Dickey & Pierce, P.L.C.

(57) ABSTRACT

One or more example embodiments of the present invention relates to a system for detection of x-ray radiation. The system comprises photon-counting x-ray CT scanners and associated edge devices. Each edge device determines a quality indicator indicative of a quality of the sensor data based on scanner data. Further, each edge device generates a parameterized machine learning model by optimizing the quality indicator. A server device receives the generated parameterized machine learning models from the edge devices, aggregates the parameterized machine learning models into an aggregated parameterized machine learning model, and sends at least part of the aggregated parameterized machine learning model back to the edge devices.

20 Claims, 2 Drawing Sheets

(56) References Cited

U.S. PATENT DOCUMENTS

| | | | |
|---|---|---|---|
| 2023/0103195 A1* | 3/2023 | Schrapp | A61B 6/5205 378/1 |
| 2023/0196571 A1* | 6/2023 | Regensburger | G06T 11/006 382/132 |
| 2024/0032884 A1* | 2/2024 | Miyazaki | A61B 6/032 |

FOREIGN PATENT DOCUMENTS

| | | | |
|---|---|---|---|
| EP | 3795082 A1 | 3/2021 | |
| EP | 3839577 A1 | 6/2021 | |
| EP | 3842839 A1 | 6/2021 | |

* cited by examiner

X-RAY RADIATION DETECTION

CROSS-REFERENCE TO RELATED APPLICATION(S)

The present application claims priority under 35 U.S.C. § 119 to European Patent Application No. EP 21200175.4, filed Sep. 30, 2021, the entire contents of which are incorporated herein by reference.

FIELD

One or more example embodiments relates to a system and to a method for detection of x-ray radiation. One or more example embodiments further relates to an edge device coupled to a photon-counting x-ray computed tomography (CT) scanner, and to a photon-counting x-ray CT scanner.

STATE OF THE ART

CT scanners comprise rotating x-ray sources and detectors placed in a gantry that measure the x-rays after passing through the body of a patient. The x-rays are attenuated by different tissues inside the body of the patient. CT scanners can thus provide detailed images of the body for diagnostic purposes.

Known CT systems comprise solid-state scintillation detectors. In the detectors, the x-rays are converted into visible light. In a further step, the light is converted into electrical signals by photodiodes attached to the backside of the detector cells.

Another approach uses photon-counting detectors which can directly transform x-ray photons into electrical signals without the intermediate step of converting x-rays into visible light. A photon-counting detector absorbs x-rays and electron-hole pairs are generated in a semiconductor. A strong electric field is applied to separate the charges.

A method for photon-counting detection of x-ray radiation using at least one direct conversion detector is known from U.S. Pat. No. 9,164,183 B2.

Compared to solid-state scintillation detectors, photon-counting detectors can avoid optical crosstalk. Accordingly, the geometric dose efficiency increases as compared to solid-state scintillation detectors. To increase the spatial resolution, detectors may be divided into smaller sub-pixels that can be read out separately.

The photon-counting technology provides an unprecedent amount of data and a new background to be developed with regard to the adequate configuration of the system parameters so that optimal settings can be standardized or defined.

CT Scanners, however, are complex systems composed of hundreds of components and have a high sensitivity to differences in parametrization, environmental changes, etc. In order to improve quality outcomes and, at the same time, patient and staff safety, several parameters must be configured and optimized.

It is however a difficult task to determine the optimal configuration parameters for a specific use case in such a multi-parameter environment.

For standard scintillation-detector-based CT systems, standard protocols and system parametrizations are known. The photon-counting technology and the availability of such a large amount of data can lead to a considerable improvement of knowledge in several areas that can improve the overall CT image quality and at the same time, reduce the risks associated to x-rays.

Conventionally, if the image of a CT system is not satisfactory, an experienced service technician close to the system is given the task to find out the source of the problem. The service technician may trace the problem back to hardware or software issues or, due to the complexity of the system, configuration issues.

The service technician can rely on logfiles, i.e., messages generated by several system peripherals that are used to track system events or the system's performance. The service technician may also use conventional test tools, that is external tools or software used to test the system.

Further, the service technician may use the results of quality tests, i.e., self tests made by the system to detect known anomalies. Further, the service technician may rely on an observation of the system, based on his or her experience. The service technician may also have knowledge about the site workflow.

Importantly, in several cases, a system parametrization may be the root cause of artifacts or low image quality. Although the different tools mentioned above can be used, the sensitivity or specificity for error detection is not 100%, leading the engineers to several trial-and-error approaches and increasing the cost of maintenance with travel costs, spare part consumption, salaries and also decreasing the system uptime, thereby creating loss of profit to the customer.

SUMMARY

Despite all the possible advantages of analyzing the amounts of data provided by the new photon-counting detectors, it is impractical, due to high volume and necessary environment, to transfer and analyze such amounts of raw data in a remote server. In practice, there are further several restrictions which do not allow the transfer of data comprising Patient Handling Information (PHI) or Patient Identifiable Information (PII).

One or more example embodiments of the present invention provides a system and a method for detection of x-ray radiation with an improved evaluation of the sensor data generated by photon-counting x-ray CT scanners.

One or more example embodiments of the present invention provides a system and a method for detection of x-ray radiation, an edge device, and a photon-counting x-ray CT scanner as recited in the independent claims. Advantageous embodiments are set out in the dependent claims.

According to one or more example embodiments, a system for detection of x-ray radiation includes a plurality of photon-counting x-ray CT scanners, each photon-counting x-ray CT scanner including an x-ray source configured to emit x-ray radiation and a plurality of photon-counting detectors configured to detect the x-ray radiation and to generate sensor data based on the detected x-ray radiation; a plurality of edge devices, wherein each edge device is coupled to an associated photon-counting x-ray CT scanner and is configured to receive scanner data from the associated photon-counting x-ray CT scanner, the scanner data comprising at least part of the sensor data from the associated photon-counting x-ray CT scanner, each edge device being configured to determine a quality indicator indicative of a quality of the sensor data from the associated photon-counting x-ray CT scanner based on the received scanner data, and each edge device being further configured to generate a parameterized machine learning model by optimizing the quality indicator, the edge device being configured to provide at least part of the received scanner data as input data to the parameterized machine learning model, the parameterized machine learning model providing information regarding the associated photon-counting x-ray CT scanner as output data; and a server device coupled to the plurality of edge devices and configured to receive the generated parameterized machine learning models from the edge devices, the server device being further configured to aggregate the parameterized machine learning models into an aggregated parameterized machine learning model, and to send at least part of the aggregated parameterized machine learning model back to the plurality of edge devices.

According to one or more example embodiments, the scanner data further comprises environmental data relating to an environment of the associated photon-counting x-ray CT scanner.

According to one or more example embodiments, the edge devices are configured to provide at least part of the information regarding the photon-counting x-ray CT scanner generated by the associated parameterized machine learning model to a user.

According to one or more example embodiments, the information regarding the associated photon-counting x-ray CT scanner provided by the associated parameterized machine learning model as output data comprises a state of health of at least one component of the associated photon-counting x-ray CT scanner.

According to one or more example embodiments, the information regarding the associated photon-counting x-ray CT scanner provided by the associated parameterized machine learning model as output data comprises at least one configuration parameter of the associated photon-counting x-ray CT scanner.

According to one or more example embodiments, at least one edge device is configured to output the at least one configuration parameter of the associated photon-counting x-ray CT scanner to a user, to receive a selection signal from the user, and to configure the associated photon-counting x-ray CT scanner according to the at least one configuration parameter, if the edge device receives the selection signal from the user.

According to one or more example embodiments, at least one edge device is configured to output an error signal to a user based on the information regarding the associated photon-counting x-ray CT scanner provided by the associated parameterized machine learning model as output data.

According to one or more example embodiments, the server device is configured to aggregate the parameterized machine learning models into the aggregated parameterized machine learning model based on the quality indicators of the parameterized machine learning models.

According to one or more example embodiments, the server device is configured to select the parameterized machine learning model with the highest quality indicator as the aggregated parameterized machine learning model.

According to one or more example embodiments, an edge device coupled to an associated photon-counting x-ray CT scanner, the photon-counting x-ray CT scanner comprising an x-ray source configured to emit x-ray radiation, and a plurality of photon-counting detectors configured to detect the x-ray radiation and to generate sensor data based on the detected x-ray radiation, the edge device includes an interface configured to receive scanner data from the associated photon-counting x-ray CT scanner, the scanner data including at least part of sensor data of the associated photon-counting x-ray CT scanner; and a computing device configured to determine a quality indicator indicative of a quality of the sensor data based on the scanner data, the computing device being further configured to generate a parameterized machine learning model by optimizing the quality indicator and to provide at least part of the scanner data as input data to the parameterized machine learning model, and the parameterized machine learning model providing information regarding the associated photon-counting x-ray CT scanner as output data, wherein the interface is further configured to provide the generated parameterized machine learning model to a server device and to receive at least part of an aggregated parameterized machine learning model generated by the server device.

According to one or more example embodiments, a photon-counting x-ray CT scanner includes the edge device.

According to one or more example embodiments, a method for detection of x-ray radiation includes emitting, by photon-counting x-ray CT scanners, x-ray radiation, detecting the x-ray radiation and generating sensor data based on the detecting; receiving, by edge devices coupled to associated photon-counting x-ray CT scanners, respectively, scanner data from the associated photon-counting x-ray CT scanner, wherein the scanner data comprises at least part of the sensor data from the associated photon-counting x-ray CT scanner; determining, by each edge device, a quality indicator indicative of a quality of the sensor data based on the scanner data; generating, by each edge device, a parameterized machine learning model by optimizing the quality indicator, at least part of the received scanner data being provided as input data to the parameterized machine learning model, the parameterized machine learning model providing information regarding the associated photon-counting x-ray CT scanner as output data; receiving, by a server device, the generated parameterized machine learning models from the edge devices; aggregating, by the server device, the parameterized machine learning models into an aggregated parameterized machine learning model; and sending, by the server device, at least part of the aggregated parameterized machine learning model back to the plurality of edge devices.

According to one or more example embodiments, the method includes providing, by at least one of the edge devices, at least part of the information regarding the associated photon-counting x-ray CT scanner generated by associated the parameterized machine learning model to a user.

According to one or more example embodiments, the method includes outputting, by at least one of the edge devices, an error signal to a user based on the information regarding the associated photon-counting x-ray CT scanner provided by the associated parameterized machine learning model as output data.

According to one or more example embodiments, the aggregating aggregates the parameterized machine learning models into the aggregated parameterized machine learning model based on the quality indicators of the parameterized machine learning models.

BRIEF DESCRIPTION OF THE DRAWINGS

The invention will be explained in greater detail with reference to exemplary embodiments depicted in the drawings as appended.

The accompanying drawings are included to provide a further understanding of the present invention and are incorporated in and constitute a part of this specification.

Other embodiments of the present invention and many of the intended advantages of the present invention will be readily appreciated as they become better understood by reference to the following detailed description. It should be understood that method steps are numbered for easier reference but that said numbering does not necessarily imply steps being performed in that order unless explicitly or implicitly described otherwise. In particular, steps may also be performed in a different order than indicated by their numbering. Some steps may be performed simultaneously or in an overlapping manner.

Figure 1:
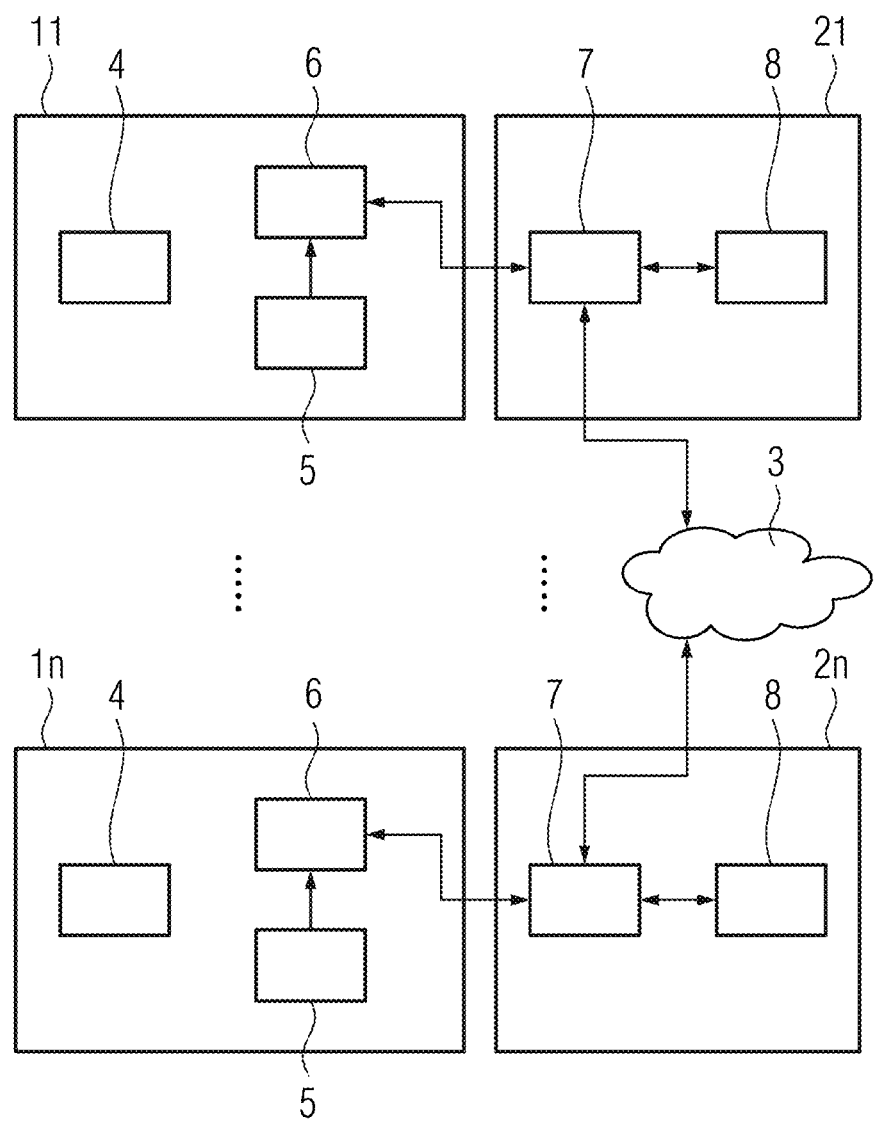
Figure 2:
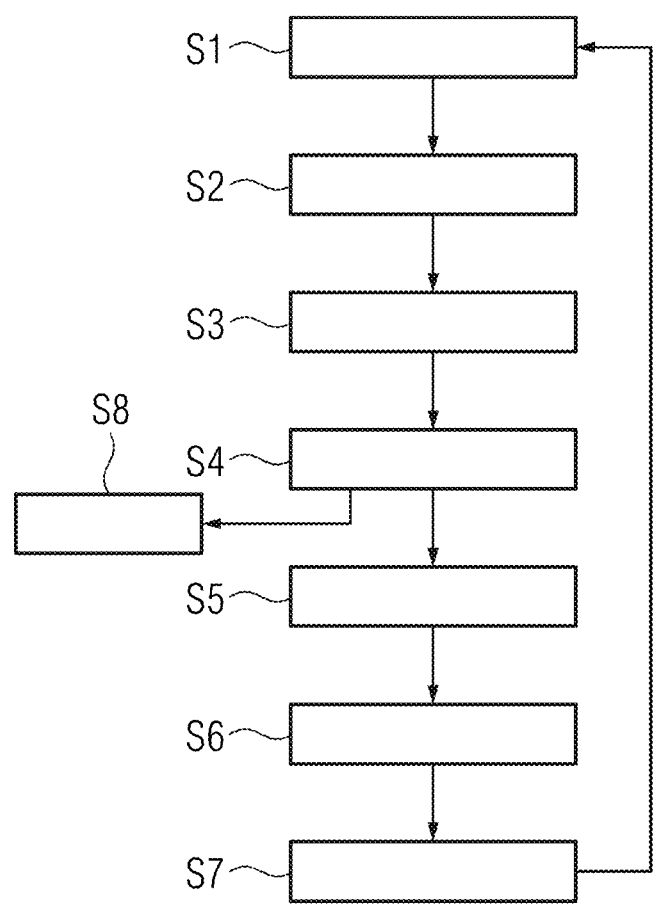

FIG. 1 schematically shows a block diagram illustrating a system for detection of x-ray radiation according to an embodiment of the invention; and FIG. 2 schematically shows a flow diagram illustrating a method for detection of x-ray radiation according to an embodiment of the invention.

DETAILED DESCRIPTION

According to the first aspect, one or more example embodiments of the present invention provides a system for detection of x-ray radiation. The system comprises a plurality of photon-counting x-ray CT scanners, wherein each photon-counting x-ray CT scanner comprises an x-ray source configured to emit x-ray radiation, and a plurality of photon-counting detectors configured to detect the x-ray radiation and to generate sensor data based on the detection. The system further comprises a plurality of edge devices, wherein each edge device is coupled to an associated photon-counting x-ray CT scanner and is configured to receive scanner data from the associated photon-counting x-ray CT scanner, wherein the scanner data comprises at least part of the sensor data. Each edge device is configured to determine a quality indicator indicative of a quality of the sensor data based on the scanner data. Further, each edge device is configured to generate a parameterized machine learning model by optimizing the quality indicator, wherein the edge device is configured to provide at least part of the scanner data as input data to the machine learning model, and wherein the machine learning model provides information regarding the photon-counting x-ray CT scanner as output data. The system further comprises a server device coupled to the plurality of edge devices and configured to receive the generated parameterized machine learning models from the edge devices, to aggregate the parameterized machine learning models into an aggregated parameterized machine learning model, and to send at least part of the aggregated parameterized machine learning model back to the plurality of edge devices.

According to the second aspect, one or more example embodiments of the present invention provides an edge device coupled to an associated photon-counting x-ray CT scanner, the photon-counting x-ray CT scanner comprising an x-ray source configured to emit x-ray radiation, and a plurality of photon-counting detectors configured to detect the x-ray radiation and to generate sensor data based on the detection. The edge device comprises an interface configured to receive scanner data from the associated photon-counting x-ray CT scanner, wherein the scanner data comprises at least part of sensor data of the associated photon-counting x-ray CT scanner. The edge device further comprises a computing device configured to determine a quality indicator indicative of a quality of the sensor data based on the scanner data, and to generate a parameterized machine learning model by optimizing the quality indicator, wherein the computing device is configured to provide at least part of the scanner data as input data to the machine learning model. The machine learning model provides information regarding the photon-counting x-ray CT scanner as output data. The interface is further configured to provide the generated parameterized machine learning model to a server device and to receive at least part of an aggregated parameterized machine learning model generated by the server device.

According to a third aspect, one or more example embodiments of the present invention provides a photon-counting x-ray CT scanner comprising an edge device according to one or more example embodiments of the present invention.

According to fourth aspect, one or more example embodiments of the present invention provides a method for detection of x-ray radiation. Photon-counting x-ray CT scanners emit x-ray radiation, detect the x-ray radiation and generate sensor data based on the detection. Edge devices coupled to associated photon-counting x-ray CT scanners receive scanner data from the associated photon-counting x-ray CT scanner, wherein the scanner data comprises at least part of the sensor data. The edge devices determine a quality indicator indicative of a quality of the sensor data based on the scanner data. The edge devices generate a parameterized machine learning model by optimizing the quality indicator, wherein at least part of the scanner data is provided as input data to the machine learning model, and wherein the machine learning model provides information regarding the photon-counting x-ray CT scanner as output data. A server device receives the generated parameterized machine learning models from the edge devices. The server device aggregates the parameterized machine learning models into an aggregated parameterized machine learning model. The server device sends at least part of the aggregated parameterized machine learning model back to the plurality of edge devices.

One or more example embodiments of the present invention provides a federated learning (FL) approach. The server device acts as an FL server which can receive data from a plurality of edge devices. Moreover, the edge devices carry out a considerable fraction of the required calculations. By analyzing the sensor data received by the scanners locally, it is possible to avoid transferring large amount of data. Therefore, the size of the server architecture can be kept small. Moreover, legal restrictions can be obeyed, because preferably neither Patient Handling Information (PHI) nor Patient Identifiable Information (PII) will be transferred to the server device. The server device preferably receives from the edge device only quality indicators (e.g., key performance indicators, KPIs) and technical results such as aggregated data, models, pattern matches, and the like. By providing only legally allowable and relevant information to the server device, data transfer can be reduced.

By generating an aggregated parameterized machine learning model, based on data received from all the photon-counting x-ray CT scanners of the system, the scanning quality can improve.

An advantage of the FL-based approach is that the knowledge of parameters related to the quality of the sensor data increases.

Further, service costs can be reduced by having the ability of diagnosing less than optimal parameters in the used models.

One or more example embodiments of the present invention provides a local calculation (raw data processing) of quality indicators, which can be collected centrally for further comparison to other systems, so that new standards can be defined and then updated to the systems for improved parametrization.

Considering the human speed and scarce availability of experts, machine learning models can help to analyze the system parameters regarding the photon-counting technology. The parameters can be compared and better understood by a mix of artificial intelligence, big data (a server device coupled to multiple edge devices) and machine learning, therefore providing augmented analytics that can lead to KPIs as a method to evaluate image quality influencing factors.

KPIs are correlated with factors influencing the image quality. The influencing factors can be hardware, software, the system configuration or a differentiation between images used and images deleted by a user. The image quality is analyzed in view of influencing factors, so that a parametrization improvement can be suggested.

By teaching the system with good and poor-quality images, it is possible to identify similar system parametrizations and define good or bad models (protocols).

According to one or more example embodiments of the present invention, a "photon-counting" x-ray CT scanner relates to a device which can directly transform x-ray photons into electrical signals, i.e., without an intermediate step of converting x-rays into visible light.

According to one or more example embodiments of the present invention, an "edge device" is a device located at the site of the corresponding photon-counting x-ray CT scanner (which defines the edge of the system).

In a further embodiment of the system for detection of x-ray radiation, the quality indicator can comprise at least one KPI.

In a further embodiment of the system for detection of x-ray radiation, the scanner data further comprises environmental data relating to an environment of the photon-counting x-ray CT scanner. The environmental data may comprise a temperature or humidity at the place of the photon-counting x-ray CT scanner which can be obtained by a server of the photon-counting x-ray CT scanner.

In a further embodiment of the system for detection of x-ray radiation, the edge devices are configured to provide at least part of the information regarding the photon-counting x-ray CT scanner generated by the machine learning model to a user. The information may be provided on a screen of the system.

In a further embodiment of the system for detection of x-ray radiation, the information regarding the photon-counting x-ray CT scanner provided by the machine learning model as output data comprises a state of health of at least one component of the photon-counting x-ray CT scanner. The information may also comprise a time to live of the components or some other degradation state information.

In a further embodiment of the system for detection of x-ray radiation, the information regarding the photon-counting x-ray CT scanner provided by the machine learning model as output data comprises at least one configuration parameter of the photon-counting x-ray CT scanner. The configuration parameters might comprise at least one of a voltage of the photon-counting x-ray CT scanner, a current of the photon-counting x-ray CT scanner, a rotation speed of the x-ray source of the photon-counting x-ray CT scanner, a slice thickness and window adjustments. The edge device may suggest key parameters which could affect the performance of the photon-counting x-ray CT scanner. The system can therefore help the user to find optimized settings.

In a further embodiment, the system for detection of x-ray radiation may comprise a real-time monitoring dashboard, also allowing actions to be triggered regarding the correction of the system behavior.

In a further embodiment of the system for detection of x-ray radiation, the edge device is configured to output the at least one configuration parameter of the photon-counting x-ray CT scanner to a user, to receive a selection signal from the user, and to configure the photon-counting x-ray CT scanner according to the at least one configuration parameter, if the edge device receives the selection signal from the user. The system therefore provides the user with a suggestion for a configuration of the photon-counting x-ray CT scanner.

In a further embodiment of the system for detection of x-ray radiation, the edge device is configured to output an error signal to a user based on the information regarding the photon-counting x-ray CT scanner provided by the machine learning model as output data. For example, if the quality indicator is below a threshold, the edge device may output the error signal.

In a further embodiment of the system for detection of x-ray radiation, the edge device may detect that the optimal machine learning model (aggregated parameterized machine learning model) produces non-optimal data, e.g., the quality indicator is smaller than a predefined threshold. The edge device may then output an error message predicting a failure.

In a further embodiment of the system for detection of x-ray radiation, the server device is configured to aggregate the parameterized machine learning models into the aggregated parameterized machine learning model based on the quality indicators of the parameterized machine learning models.

In a further embodiment of the system for detection of x-ray radiation, the server device is configured to select the parameterized machine learning model with the highest quality indicator as the aggregated parameterized machine learning model.

In a further embodiment of the system for detection of x-ray radiation, the system comprises available system performance dashboards for the user to track system statuses like uptime, planned downtime and/or unplanned downtime.

In a further embodiment of the method for detection of x-ray radiation, the edge devices provide at least part of the information regarding the photon-counting x-ray CT scanner generated by the machine learning model to a user.

In a further embodiment of the method for detection of x-ray radiation, the edge devices output an error signal to a user based on the information regarding the photon-counting x-ray CT scanner provided by the machine learning model as output data.

In a further embodiment of the method for detection of x-ray radiation, the server device aggregates the parameterized machine learning models into the aggregated parameterized machine learning model based on the quality indicators of the parameterized machine learning models.

FIG. 1 schematically shows a block diagram illustrating a system for detection of x-ray radiation. The system comprises a plurality of photon-counting x-ray CT scanners 11 to 1n, wherein n denotes an integer greater than 1. The invention is not restricted to a specific number of photon-counting x-ray CT scanners 11 to 1n.

Each photon-counting x-ray CT scanner 11 to 1n comprises an x-ray source 4 which emits x-ray radiation, and a plurality of photon-counting detectors 5 that detect the x-ray radiation and generate sensor data based on the detection. The x-ray source 4 can rotate and the detectors 5 measure the x-rays after passing through the body of the patient. The sensor data depends on body tissues of the patient but also on environmental data, such as a temperature or humidity at the site of the photon-counting x-ray CT scanner 11 to 1n. Each photon-counting detector 5 absorbs x-rays and transforms x-ray photons into electrical signals (sensor data).

Interfaces 6 of the photon-counting x-ray CT scanners 11 to 1n are connected to an interface 7 of an edge device 21 to 2n associated with the respective photon-counting x-ray CT scanner 11 to 1n.

The edge devices 21 to 2n are located at the site of the associated photon-counting x-ray CT scanner 11 to 1n. According to an embodiment, an edge device 21 to 2n may be integrated into the photon-counting x-ray CT scanner 11 to 1n, e.g., arranged in a common compartment.

Each edge device 21 to 2n receives scanner data from the associated photon-counting x-ray CT scanner 11 to 1n. The scanner data comprises part or all of the sensor data. The scanner data may also comprise environmental data, e.g., information about a temperature or humidity at the site of the photon-counting x-ray CT scanner 11 to 1n.

Each edge device 21 to 2n comprises a computing device 8.

The computing device 8 as well as some or all components of the system may comprise hardware and software components. The hardware components may comprise at least one of microcontrollers, central processing units (CPU), memories and storage devices.

The computing device 8 determines a quality indicator indicative of a quality of the sensor data based on the scanner data. Further, the computing device 8 of each edge device 21 to 2n generates a parameterized machine learning model by optimizing the quality indicator. The computing device 8 provides at least part of the scanner data as input data to the machine learning model. The machine learning model provides information regarding the photon-counting x-ray CT scanner 11 to 1n as output data. The information may comprise a state of health or a time to live of one or more components of the associated photon-counting x-ray CT scanner 11 to 1n. Additionally or alternatively, the information may comprise one or more configuration parameters of the associated photon-counting x-ray CT scanner 11 to 1n. The configuration parameter may relate to at least one of a voltage of the associated photon-counting x-ray CT scanner 11 to 1n, a current of the associated photon-counting x-ray CT scanner 11 to 1n, a rotation speed of the x-ray source of the associated photon-counting x-ray CT scanner 11 to 1n, a slice-thickness and window adjustments.

The system further comprises a server device 3 coupled to the edge devices 21 to 2n. The server device 3 is located remotely and may comprise a plurality of physical units, possibly located at different sites. The server device 3 receives the generated parameterized machine learning models from the edge devices 21 to 2n. For example, the edge devices 21 to 2n may send information regarding a type of machine learning model and information regarding parameters of the machine learning model to the server device 3.

The machine learning model may comprise a support vector machine, a decision tree model, an artificial neural network, and the like.

The server device 3 aggregates the parameterized machine learning models obtained by the edge devices 21 to 2n into an aggregated parameterized machine learning model. The server device 3 is a federated learning server. The server device 3 may generate the aggregated parameterized machine learning model based on the quality indicators. The quality indicators can be used as weights and the aggregated parameterized machine learning model can be determined by weighting the characterized machine learning models based on the quality indicators. According to another embodiment, the server device 3 selects the parameterized machine learning model with the highest quality indicator as the aggregated parameterized machine learning model.

The server device 3 sends at least part of the aggregated parameterized machine learning model back to the plurality of edge devices 21 to 2n. For example, the server device 3 may send at least some of the parameters of the aggregated parameterized machine learning model to the edge devices 21 to 2n.

According to an embodiment, the server device 3 sends at least part of the aggregated parameterized machine learning model back to an edge device 21 to 2n each time the server device 3 receives a generated parameterized machine learning model from the edge device 21 to 2n. According to a further embodiment, the server device 3 can also send at least part of the aggregated parameterized machine learning model back to an edge device 21 to 2n at predefined time points, e.g., after a predefined time span. For example, the server device 3 may provide the at least part of the aggregated parameterized machine learning model once per day, once per week or the like.

The edge devices 21 to 2n may then update the parameterized machine learning model computed locally based on the received aggregated parameterized machine learning model. The edge devices 21 to 2n may use the aggregated parameterized machine learning model for further processing data from the photon-counting x-ray CT scanners 11 to 1n.

FIG. 2 schematically shows a flow diagram illustrating a method for detection of x-ray radiation.

In a method step S1, photon-counting x-ray CT scanners 11 to 1n emit x-ray radiation, detect the x-ray radiation and generate sensor data based on the detection.

In a method step S2, edge devices 21 to 2n coupled to associated photon-counting x-ray CT scanners 11 to 1n receive scanner data from the associated photon-counting x-ray CT scanner 11 to 1n, wherein the scanner data comprises at least part of the sensor data. The scanner data may further comprise environmental data regarding the environment of the photon-counting x-ray CT scanner 11 to 1n.

In a method step S3, the edge devices 21 to 2n determine a quality indicator indicative of a quality of the sensor data based on the scanner data. The quality indicator can comprise at least one of an image quality, a signal-to-noise ratio (SNR), a contrast-to-noise ratio (CNR), a number of deleted images and a number of repeated examinations.

In a method step S4, the edge devices 21 to 2n generate a parameterized machine learning model by optimizing the quality indicator, wherein at least part of the scanner data is provided as input data to the machine learning model, and wherein the machine learning model provides information regarding the photon-counting x-ray CT scanner 11 to 1n as output data.

Optionally, the edge device 21 to 2n provides information to a user based on the output data, step S8. For example, the edge device 21 to 2n may suggest the generated parameterized machine learning model to the user. The user can decide to use the model or to not use the model. The edge device 21 to 2n can also send an error message to the user, for example if the quality indicator is smaller than a predefined threshold.

The edge device 21 to 2n can therefore provide both data processing functions and system monitoring functions. With regard to data processing, the edge device 21 to 2n may process physical parameters like sensor data (raw data of the photon-counting x-ray CT scanners 11 to 1n), voltages, currents, rotational speeds, slice-thicknesses, window adjustments, contrast data, humidity, temperature, etc.

In a method step S5, the edge devices 21 to 2n send the generated parameterized machine learning models to a server device 3 which receives and stores the generated parameterized machine learning models. The parametrization of each model and the outcoming image quality as defined by the quality indicator is stored in the server device 3 in order to compare all generated machine learning models with each other. The server device 3 may also group machine learning models by system type or another entity, since the behavior between such entities might be different.

In a method step S6, the server device 3 aggregates the parameterized machine learning models into an aggregated parameterized machine learning model.

In a method step S7, the server device 3 sends at least part of the aggregated parameterized machine learning model back to the plurality of edge devices 21 to 2n.

The edge device 21 to 2n can update the parameterized machine learning model computed locally based on the received aggregated parameterized machine learning model. The edge devices 21 to 2n may use the aggregated parameterized machine learning model for further processing data from the photon-counting x-ray CT scanners 11 to 1n.

It should be understood that all advantageous options, variance in modifications described herein and the foregoing with respect to embodiments of the system for detection of x-ray radiation may be equally applied to embodiments of the method for detection of x-ray radiation, and vice versa.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules.

Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

In the foregoing detailed description, various features are grouped together in one or more examples for the purpose of streamlining the disclosure. It is to be understood that the above description is intended to be illustrative, and not restrictive. It is intended to cover alternatives, modifications and equivalents. Many other examples will be apparent to one skilled in the art upon reviewing the above specification.

We claim:

1. A system for detection of x-ray radiation, comprising:
   a plurality of photon-counting x-ray CT scanners, each photon-counting x-ray CT scanner including an x-ray source configured to emit x-ray radiation and a plurality of photon-counting detectors configured to detect the x-ray radiation and to generate sensor data based on the detected x-ray radiation;
   a plurality of edge devices, wherein each edge device is coupled to an associated photon-counting x-ray CT scanner and is configured to receive scanner data from the associated photon-counting x-ray CT scanner, the scanner data comprising at least part of the sensor data from the associated photon-counting x-ray CT scanner, each edge device being configured to determine a quality indicator indicative of a quality of the sensor data from the associated photon-counting x-ray CT scanner based on the received scanner data, and each edge device being further configured to generate a parameterized machine learning model by optimizing the quality indicator, the edge device being configured to provide at least part of the received scanner data as input data to the parameterized machine learning model, the parameterized machine learning model providing information regarding the associated photon-counting x-ray CT scanner as output data; and
   a server device coupled to the plurality of edge devices and configured to receive the generated parameterized machine learning models from the edge devices, the server device being further configured to aggregate the parameterized machine learning models into an aggregated parameterized machine learning model, and to send at least part of the aggregated parameterized machine learning model back to the plurality of edge devices.

2. The system of claim 1, wherein the scanner data further comprises environmental data relating to an environment of the associated photon-counting x-ray CT scanner.

3. The system of claim 2, wherein the information regarding the associated photon-counting x-ray CT scanner provided by the associated parameterized machine learning model as output data comprises a state of health of at least one component of the associated photon-counting x-ray CT scanner.

4. The system of claim 1, wherein the edge devices are configured to provide at least part of the information regarding the photon-counting x-ray CT scanner generated by the associated parameterized machine learning model to a user.

5. The system of claim 4, wherein the information regarding the associated photon-counting x-ray CT scanner provided by the associated parameterized machine learning model as output data comprises a state of health of at least one component of the associated photon-counting x-ray CT scanner.

6. The system of claim 1, wherein the information regarding the associated photon-counting x-ray CT scanner provided by the associated parameterized machine learning model as output data comprises a state of health of at least one component of the associated photon-counting x-ray CT scanner.

7. The system of claim 6, wherein the server device is configured to aggregate the parameterized machine learning models into the aggregated parameterized machine learning model based on the quality indicators of the parameterized machine learning models.

8. The system of claim 7, wherein the server device is configured to select the parameterized machine learning model with the highest quality indicator as the aggregated parameterized machine learning model.

9. The system of claim 6, wherein the information regarding the associated photon-counting x-ray CT scanner provided by the associated parameterized machine learning model as output data comprises at least one configuration parameter of the associated photon-counting x-ray CT scanner.

10. The system of claim 1, wherein the information regarding the associated photon-counting x-ray CT scanner provided by the associated parameterized machine learning model as output data comprises at least one configuration parameter of the associated photon-counting x-ray CT scanner.

11. The system of claim 1, wherein at least one edge device is configured to output the at least one configuration parameter of the associated photon-counting x-ray CT scanner to a user, to receive a selection signal from the user, and to configure the associated photon-counting x-ray CT scanner according to the at least one configuration parameter, if the edge device receives the selection signal from the user.

12. The system of claim 1, wherein at least one edge device is configured to output an error signal to a user based on the information regarding the associated photon-counting x-ray CT scanner provided by the associated parameterized machine learning model as output data.

13. The system of claim 1, wherein the server device is configured to aggregate the parameterized machine learning models into the aggregated parameterized machine learning model based on the quality indicators of the parameterized machine learning models.

14. The system of claim 13, wherein the server device is configured to select the parameterized machine learning model with the highest quality indicator as the aggregated parameterized machine learning model.

15. An edge device coupled to an associated photon-counting x-ray CT scanner, the photon-counting x-ray CT scanner comprising an x-ray source configured to emit x-ray radiation, and a plurality of photon-counting detectors configured to detect the x-ray radiation and to generate sensor data based on the detected x-ray radiation, the edge device comprising:
- an interface configured to receive scanner data from the associated photon-counting x-ray CT scanner, the scanner data including at least part of sensor data of the associated photon-counting x-ray CT scanner; and
- a computing device configured to determine a quality indicator indicative of a quality of the sensor data based on the scanner data, the computing device being further configured to generate a parameterized machine learning model by optimizing the quality indicator and to provide at least part of the scanner data as input data to the parameterized machine learning model, and the parameterized machine learning model providing information regarding the associated photon-counting x-ray CT scanner as output data,
- wherein the interface is further configured to provide the generated parameterized machine learning model to a server device and to receive at least part of an aggregated parameterized machine learning model generated by the server device.

16. A photon-counting x-ray CT scanner comprising the edge device of claim 15.

17. A method for detection of x-ray radiation, the method comprising:
- emitting, by photon-counting x-ray CT scanners, x-ray radiation, detecting the x-ray radiation and generating sensor data based on the detecting;
- receiving, by edge devices coupled to associated photon-counting x-ray CT scanners, respectively, scanner data from the associated photon-counting x-ray CT scanner, wherein the scanner data comprises at least part of the sensor data from the associated photon-counting x-ray CT scanner;
- determining, by each edge device, a quality indicator indicative of a quality of the sensor data based on the scanner data;
- generating, by each edge device, a parameterized machine learning model by optimizing the quality indicator, at least part of the received scanner data being provided as input data to the parameterized machine learning model, the parameterized machine learning model providing information regarding the associated photon-counting x-ray CT scanner as output data;
- receiving, by a server device, the generated parameterized machine learning models from the edge devices;
- aggregating, by the server device, the parameterized machine learning models into an aggregated parameterized machine learning model; and
- sending, by the server device, at least part of the aggregated parameterized machine learning model back to the plurality of edge devices.

18. The method of claim 17, further comprising:
- providing, by at least one of the edge devices, at least part of the information regarding the associated photon-counting x-ray CT scanner generated by associated the parameterized machine learning model to a user.

19. The method of claim 17, further comprising:
- outputting, by at least one of the edge devices, an error signal to a user based on the information regarding the associated photon-counting x-ray CT scanner provided by the associated parameterized machine learning model as output data.

20. The method of claim 17, wherein the aggregating aggregates the parameterized machine learning models into the aggregated parameterized machine learning model based on the quality indicators of the parameterized machine learning models.

* * * * *